(12) United States Patent
Yudovich et al.

(10) Patent No.: US 11,205,501 B2
(45) Date of Patent: Dec. 21, 2021

(54) DETERMINATION OF FREQUENCY DISTRIBUTION OF NUCLEOTIDE SEQUENCE VARIANTS

(71) Applicant: TIGERQ AB, Lund (SE)

(72) Inventors: David Yudovich, Lund (SE); Jonas Larsson, Lund (SE)

(73) Assignee: TIGERQ AB, Lund (SE)

( * ) Notice: Subject to any disclaimer, the term of this patent is extended or adjusted under 35 U.S.C. 154(b) by 0 days.

(21) Appl. No.: 17/043,625

(22) PCT Filed: Apr. 2, 2019

(86) PCT No.: PCT/SE2019/050299
§ 371 (c)(1),
(2) Date: Sep. 29, 2020

(87) PCT Pub. No.: WO2019/199218
PCT Pub. Date: Oct. 17, 2019

(65) Prior Publication Data
US 2021/0020268 A1 Jan. 21, 2021

(30) Foreign Application Priority Data
Apr. 11, 2018 (SE) .................................... 1850405-0

(51) Int. Cl.
*G16B 30/10* (2019.01)
(52) U.S. Cl.
CPC .................................... *G16B 30/10* (2019.02)
(58) Field of Classification Search
CPC ........ C12Q 2537/159; C12Q 2537/165; C12Q 1/6869; C12Q 2600/156; C12Q 1/6827;
(Continued)

(56) References Cited

U.S. PATENT DOCUMENTS

2015/0324519 A1* 11/2015 Liu .................. G16H 20/00
702/20
2017/0242588 A1 8/2017 Ujibashi et al.
(Continued)

FOREIGN PATENT DOCUMENTS

WO WO 2006/084391 A1 8/2006
WO WO 2015/048753 A1 4/2015
(Continued)

OTHER PUBLICATIONS

Kosugi, S et al. Coval: improving alignment quality and variant calling accuracy for next-generation sequencing data. 2013 PLOS ONE vol. 8 issue 10, e7452 and supplemental information. (Year: 2013).*

(Continued)

*Primary Examiner* — Mary K Zeman
(74) *Attorney, Agent, or Firm* — Casimir Jones, S.C.; Lisa V. Mueller

(57) ABSTRACT

Determination of a frequency distribution of nucleotide sequence variants—differing from a nucleotide reference by at least one intermediate part—of a sample is disclosed. A reference set of sequence read data is generated by performing a plurality of reference sequence reads (each having a read start site, RSS) for each sequence reference variant of a reference variant list. It is determined (for each RSS and for the intermediate part of each sequence reference variant) whether the intermediate part is detectable by corresponding reference sequence read. A sample set of sequence read data is generated by performing sample sequence reads for the sample, and a total number of occurrences in the sample set is determined for each RSS and for the intermediate part of each sequence reference variant. The frequency distribution of the plurality of nucleotide sequence variants is deter- (Continued)

mined based on the number of occurrences determined for an RSS where the intermediate part is detectable.

7 Claims, 4 Drawing Sheets

(58) Field of Classification Search
CPC ........ C12Q 1/68; C12Q 1/6851; G16B 20/00; G16B 30/00; G16B 50/00; G16B 40/00; G16B 45/00; G16B 15/00; G16B 15/30; G16B 20/20; G16B 25/20; G16B 40/30; G16B 50/30; G16B 40/20; G16B 50/20; G16B 5/00; G16B 20/10; G16B 30/10; G16B 20/40; G16B 30/20; G16B 5/20; G16B 35/00; G16B 35/20; G16B 5/10; G16B 50/10; G16H 50/20; G16H 10/60; G16H 50/30; G16H 40/67; G16H 10/40; G16H 50/50; G16H 20/30; G16H 50/70; G16H 15/00; G16H 20/00; G16H 50/00; G16H 80/00; G16H 40/60; G16H 70/20; C40B 40/08; C40B 40/06; C40B 20/04; C40B 20/06; G06F 3/0482; G06F 16/26; G06F 16/9535; G06F 3/0237; G06F 16/906; G06F 19/00; G06F 2216/03; G06F 16/285; G06F 17/18; G06N 20/00; G06N 20/20; G06N 3/0454; G06N 3/08; G06N 5/003; G06N 5/046; G06N 20/10; G06N 7/005; G06N 5/02; G06N 5/022; G06N 5/04; G06N 3/02; G06N 3/04; G06T 2200/24; G06T 2207/20084; G16C 20/30; G16C 20/60; A61B 5/7275; A61B 5/7267; A61B 5/1118; A61B 5/6801; A61B 5/681; A61B 5/6823; A61B 5/6833; A61B 5/0002; A61B 5/02158; A61B 5/02405; A61B 5/6802; A61B 5/6824; A61B 5/6898; A61B 5/02; A61B 5/024; A61B 5/02438; A61B 5/7282; A61B 6/5217; A61B 8/02; A61B 8/5223; G01N 2800/32; G01N 33/50; G01N 27/416; G01N 2800/50; G01N 2800/60; G01N 33/48792; G06K 9/6256; G06K 9/6218; G06K 9/6262; G06K 9/6267; G06K 2209/05; G06K 9/6257; G06K 9/6271
See application file for complete search history.

(56) References Cited

U.S. PATENT DOCUMENTS

| | | | |
|---|---|---|---|
| 2017/0270245 A1* | 9/2017 | van Rooyen | G16B 30/00 |
| 2018/0121600 A1* | 5/2018 | Dilernia | G16B 30/10 |
| 2019/0348149 A1* | 11/2019 | Chen | G06F 17/18 |
| 2019/0362808 A1* | 11/2019 | Halperin | G16B 20/20 |
| 2021/0020268 A1* | 1/2021 | Yudovich | G16B 30/10 |

FOREIGN PATENT DOCUMENTS

| | | | |
|---|---|---|---|
| WO | WO 2016/005524 A1 | 1/2016 | |
| WO | WO 2016/009224 A1 | 1/2016 | |
| WO | WO 2017/085459 A1 | 5/2017 | |

OTHER PUBLICATIONS

Neuman et al. (2012) Analysis of insertion-deletion from deep sequencing data: software evaluation for optimal detection. Briefings in bioinformatics vol. 14(1) p. 46-55. (Year: 2012).*

Audano et al. (2017) Mapping-free variant calling using haplotype reconstruction from k-mer frequencies. Bioinformatics 34(10) p. 1659-1665. (Year: 2017).*

Kim (2018) Strelka2: fast and accurate calling of germline and somatic variants. Nature Methods vol. 15:591-594. (Year: 2018).*

Garrison et al. (2018) Variation graph toolkit improves read mapping by representing genetic variation in the reference. Nature biotechnology vol. 36(9) p. 875. (Year: 2018).*

Pattnaik et al. (2014) SinC: an accurate and fast error-model based simulator for SNPs, Indels and CNVs coupled with a read generator for short-read sequence data. BMC bioinformatics 15:40. (Year: 2014).*

Lai et al. (2016) VarDict: a novel and versatile variant caller for next-generation sequencing in cancer research. Nucleic Acids Research 44(11) e108. (Year: 2016).*

Hasan et al. (2015) Performance evaluation of indel calling tools using real short read data. Human Genomics vol. 9:20. (Year: 2015).*

Lee et al. (2014) MOSAIK: a hash-based algorithm for accurate next-generation sequencing short-read mapping. PLOS One 9(3) e90581. (Year: 2014).*

Boel et al., "BATCH-GE: Batch analysis of Next-Generation Sequencing data for genome editing assessment." Sci Rep. 2016, 6(30330), pp. 1-9.

Brinkman et al., "Easy quantification of template-directed CRISPR/Cas9 editing." Nucleic Acids Research, 2018, vol. 46, No. 10, e58, pp. 1-9.

Huang et al., "A novel multi-alignment pipeline for high-throughput sequencing data." Database, 2014, p. 1-12.

Tothova et al., "Multiplex CRISPR/Cas9-Based Genome Editing in Human Hematopoietic Stem Cells Models Clonal Hematopoiesis and Myeloid Neoplasia." Cell Stem Cell 2017, 21:547-555.

Ye et al., "Alignment of Short Reads: A Crucial Step for Application of Next-Generation Sequencing Data in Precision Medicine." Pharmaceutics 2015, 7: 523-541.

* cited by examiner

DETERMINATION OF FREQUENCY DISTRIBUTION OF NUCLEOTIDE SEQUENCE VARIANTS

CROSS-REFERENCE TO RELATED APPLICATIONS

This application is a national phase application under 35 U.S.C. § 371 of PCT International Application No. PCT/SE2019/050299, filed Apr. 2, 2019, which claims the benefit of Swedish Application No. 1850405-0, filed Apr. 11, 2018, each of which are herein incorporated by reference.

TECHNICAL FIELD

The present disclosure relates generally to the field of analyzing nucleotide sequence samples. More particularly, it relates to determination of frequency distribution for nucleotide sequence variants in such a sample.

BACKGROUND

When analyzing a nucleotide sequence sample—e.g., a sample of deoxyribonucleic acid (DNA) or ribonucleic acid (RNA)—it may be desirable to be able to achieve an accurate determination of the frequency distribution of nucleotide sequence variants in the sample. In particular, it may be desirable to achieve an accurate determination of the frequency distribution of nucleotide sequence variants surrounding a specific site of interest in the sample. The rest of this disclosure relates to nucleotide sequence variants surrounding such a specific site of interest (also termed target site or target position).

When referred to herein, a nucleotide sequence may have any suitable length and may comprise one or more nucleotide sequence entities. For example, a nucleotide sequence may consist of a full genome, one or more chromosomes of a genome, or one or more parts (e.g., genes) of one or more chromosomes.

For example, if an original nucleotide sequence is altered for some purpose, e.g., if a specific site is subjected to intentional modification in a gene editing process (compare e.g. with Cre combination), the nucleotide sequence sample may comprise a collection of altered nucleotide sequences. In such an example, it may be interesting to be able to accurately determine how many of the altered nucleotide sequence underwent which alteration. Accurate determination of the frequency distribution of nucleotide sequence variants in the sample would provide such results.

Existing approaches for estimation of sequence variant frequency distribution may be proved to be inaccurate; at least to some extent. Therefore, there is a need for alternative approaches for determination of sequence variant frequency distribution. Preferably, such approaches should provide increased, i.e., improved accuracy.

SUMMARY

It should be emphasized that the term "comprises/comprising" when used in this specification is taken to specify the presence of stated features, integers, steps, or components, but does not preclude the presence or addition of one or more other features, integers, steps, components, or groups thereof. As used herein, the singular forms "a", "an" and "the" are intended to include the plural forms as well, unless the context clearly indicates otherwise.

It should be noted that the term determination, when referred to herein, may include estimation according to some embodiments, where applicable.

It is an object of some embodiments to solve or mitigate, alleviate, or eliminate at least some of the above or other disadvantages.

According to a first aspect, this is achieved by a method for determining a frequency distribution of a plurality of nucleotide sequence variants of a nucleotide sequence sample, wherein the plurality of nucleotide sequence variants comprises a nucleotide reference sequence, and wherein each nucleotide sequence variant (which is not identical to the nucleotide reference sequence) differs from the nucleotide reference sequence by at least one intermediate part and coincides with the nucleotide reference sequence by at least two parts of the nucleotide reference sequence.

The method comprises generating a reference variant list of sequence reference variants comprising unique nucleotide sequence variants of the plurality of nucleotide sequence variants, and generating a reference set of sequence read data by performing a plurality of reference sequence reads for each sequence reference variant of the reference variant list, wherein each reference sequence read has a read start site (RSS).

The method also comprises (for each RSS and for the intermediate part of each sequence reference variant) determining whether or not the intermediate part is detectable by corresponding reference sequence read based on alignment of the corresponding reference sequence read to the reference variant list.

Furthermore, the method comprises generating a sample set of sequence read data by performing one or more sample sequence reads for each of a plurality of nucleotide sequence variant fragments of the nucleotide sequence sample, wherein each sample sequence read corresponds to a reference sequence read and has a corresponding RSS.

The method also comprises (for each RSS and for the intermediate part of each sequence reference variant) determining a total number of occurrences in the sample set of sequence read data based on alignment of corresponding sample sequence read to the reference variant list.

The method further comprises determining the frequency distribution of the plurality of nucleotide sequence variants based on the total number of occurrences and the determination of whether or not the intermediate part is detectable for each RSS.

It should be noted that the nucleotide sequence variants referred to herein are nucleotide sequence variants surrounding one specific site of interest of the nucleotide reference sequence. In various embodiments, the approaches herein may be generalized to determination of frequency distribution in relation to more than one specific site of interest.

Typically, RSS is defined in relation to the specific site of interest.

In some embodiments, the method may comprise (for each pair of sequence reference variants, which does not comprise the nucleotide reference sequence) determining a relative occurrence ratio between the sequence reference variants of the pair based on the number of occurrences of each of the sequence reference variants of the pair determined for an RSS where the intermediate part is detectable for each of the sequence reference variants of the pair, and determining the frequency distribution of the plurality of nucleotide sequence variants based on the relative occurrence ratios.

In some embodiments, the method further comprises defining the nucleotide reference sequence.

In some embodiments, the intermediate part is one or more of: an insertion, a deletion, an alteration, and a translocation.

In some embodiments, determining (for an RSS and for the intermediate part of a sequence reference variant) whether or not the intermediate part is detectable by corresponding reference sequence read comprises determining, via alignment, a detection correlation value for the RSS between the corresponding reference sequence read and the sequence reference variant, determining the intermediate part to be detectable at the RSS by the corresponding reference sequence read when the detection correlation value is above a detection threshold value, and determining the intermediate part to be non-detectable at the RSS by the corresponding reference sequence read when the detection correlation value is not above the detection threshold value.

In some embodiments, determining (for an RSS and for the intermediate part of a sequence reference variant) a total number of occurrences in the sample set comprises determining, via alignment, a sample correlation value for the RSS between the corresponding sample sequence read and the sequence reference variant, counting an occurrence when the sample correlation value is above an occurrence threshold value, and refraining from counting an occurrence when the sample correlation value is not above the occurrence threshold value.

In some embodiments, the method further comprises receiving an input signal indicative of one or more of the plurality of nucleotide sequence variants and the nucleotide reference sequence.

In some embodiments, the method further comprises transferring a reporting signal indicative of the frequency distribution to a user interface.

A second aspect is a computer program product comprising a non-transitory computer readable medium, having thereon a computer program comprising program instructions. The computer program is loadable into a data processing unit and configured to cause execution of the method according to the first aspect when the computer program is run by the data processing unit.

A third aspect is an apparatus for determining a frequency distribution of a plurality of nucleotide sequence variants of a nucleotide sequence sample, wherein the plurality of nucleotide sequence variants comprises a nucleotide reference sequence, and wherein each nucleotide sequence variant (which is not identical to the nucleotide reference sequence) differs from the nucleotide reference sequence by at least one intermediate part and coincides with the nucleotide reference sequence by at least two parts of the nucleotide reference sequence.

The apparatus comprises controlling circuitry configured to cause generation of a reference variant list of sequence reference variants comprising unique nucleotide sequence variants of the plurality of nucleotide sequence variants, and generation of a reference set of sequence read data by performing a plurality of reference sequence reads for each sequence reference variant of the reference variant list, wherein each reference sequence read has a read start site (RSS).

The controlling circuitry is also configured to cause (for each RSS and for the intermediate part of each sequence reference variant) determination of whether or not the intermediate part is detectable by corresponding reference sequence read based on alignment of the corresponding reference sequence read to the reference variant list.

Furthermore, the controlling circuitry is configured to cause generation of a sample set of sequence read data by performing one or more sample sequence reads for each of a plurality of nucleotide sequence variant fragments of the nucleotide sequence sample, wherein each sample sequence read corresponds to a reference sequence read and has a corresponding RSS.

The controlling circuitry is also configured to cause (for each RSS and for the intermediate part of each sequence reference variant) determination of a total number of occurrences in the sample set of sequence read data based on alignment of corresponding sample sequence read to the reference variant list.

Furthermore, the controlling circuitry is configured to cause determination of the frequency distribution of the plurality of nucleotide sequence variants based on the total number of occurrences and the determination of whether or not the intermediate part is detectable for each RSS.

In some embodiments, the controlling circuitry may be configured to cause (for each pair of sequence reference variants, which does not comprise the nucleotide reference sequence) determination of a relative occurrence ratio between the sequence reference variants of the pair based on the number of occurrences of each of the sequence reference variants of the pair determined for an RSS where the intermediate part is detectable for each of the sequence reference variants of the pair, and determination of the frequency distribution of the plurality of nucleotide sequence variants based on the relative occurrence ratios.

A fourth aspect is a server node comprising the apparatus of the third aspect.

In some embodiments, any of the above aspects may additionally have features identical with or corresponding to any of the various features as explained above for any of the other aspects.

An advantage of some embodiments is that the accuracy of the frequency distribution is increased. This is because the relative number of occurrences of the intermediate part of a variant is determined only in relation to read start sites where the intermediate part is detectable.

Some further advantages of some embodiments include one or more of:
that quantification of much larger variants is possible (typically +/−300 base pair, bp, insertions and/or deletions; compared to +/−50 when prior art approaches are applied),
that quantification is possible of variants with only single-sided matching sequence, e.g., translocations,
that a statistical quality assessment may be provided of the resulting variant frequency distribution (since all calculations may be reported with variance estimates), which in turn provides an indication of reproducibility (increasing user confidence in relation to the reported measurements), and
that depiction of fragmentation bias (and its correction) is enabled.

BRIEF DESCRIPTION OF THE DRAWINGS

Further objects, features and advantages will appear from the following detailed description of embodiments, with reference being made to the accompanying drawings. The drawings are not necessarily to scale, emphasis instead being placed upon illustrating the example embodiments.

DETAILED DESCRIPTION

As already mentioned above, it should be emphasized that the term "comprises/comprising" when used in this specification is taken to specify the presence of stated features, integers, steps, or components, but does not preclude the presence or addition of one or more other features, integers, steps, components, or groups thereof. As used herein, the singular forms "a", "an" and "the" are intended to include the plural forms as well, unless the context clearly indicates otherwise.

Embodiments of the present disclosure will be described and exemplified more fully hereinafter with reference to the accompanying drawings. The solutions disclosed herein can, however, be realized in many different forms and should not be construed as being limited to the embodiments set forth herein.

In the following, embodiments will be described where a frequency distribution is determined for a plurality of nucleotide sequence variants of a nucleotide sequence sample.

The plurality of nucleotide sequence variants comprises a nucleotide reference sequence. The nucleotide reference sequence may be predefined and received as an input to the frequency distribution determination process. Alternatively, the nucleotide reference sequence may be determined as an initial step of the frequency distribution determination process. For example, in gene editing, the original nucleotide sequence may be used as the nucleotide reference sequence or an altered nucleotide sequence may be used as the nucleotide reference sequence.

The plurality of nucleotide sequence variants further comprises other nucleotide sequence variants than the nucleotide reference sequence. The other nucleotide sequence variants are either identical to the nucleotide reference sequence or differs from the nucleotide reference sequence.

Each nucleotide sequence variant, which is not identical to the nucleotide reference sequence, differs from the nucleotide reference sequence by at least one intermediate part and coincides with the nucleotide reference sequence by at least two parts of the nucleotide reference sequence. Each intermediate part may, for example, be an insertion, a deletion, or an alteration. Another example of an intermediate part is a translocation. The latter may, for example, occur when the nucleotide reference sequence is a full genome and wherein two chromosomes are respectively broken up and erroneously cross-wise rejoined.

Figure 1:
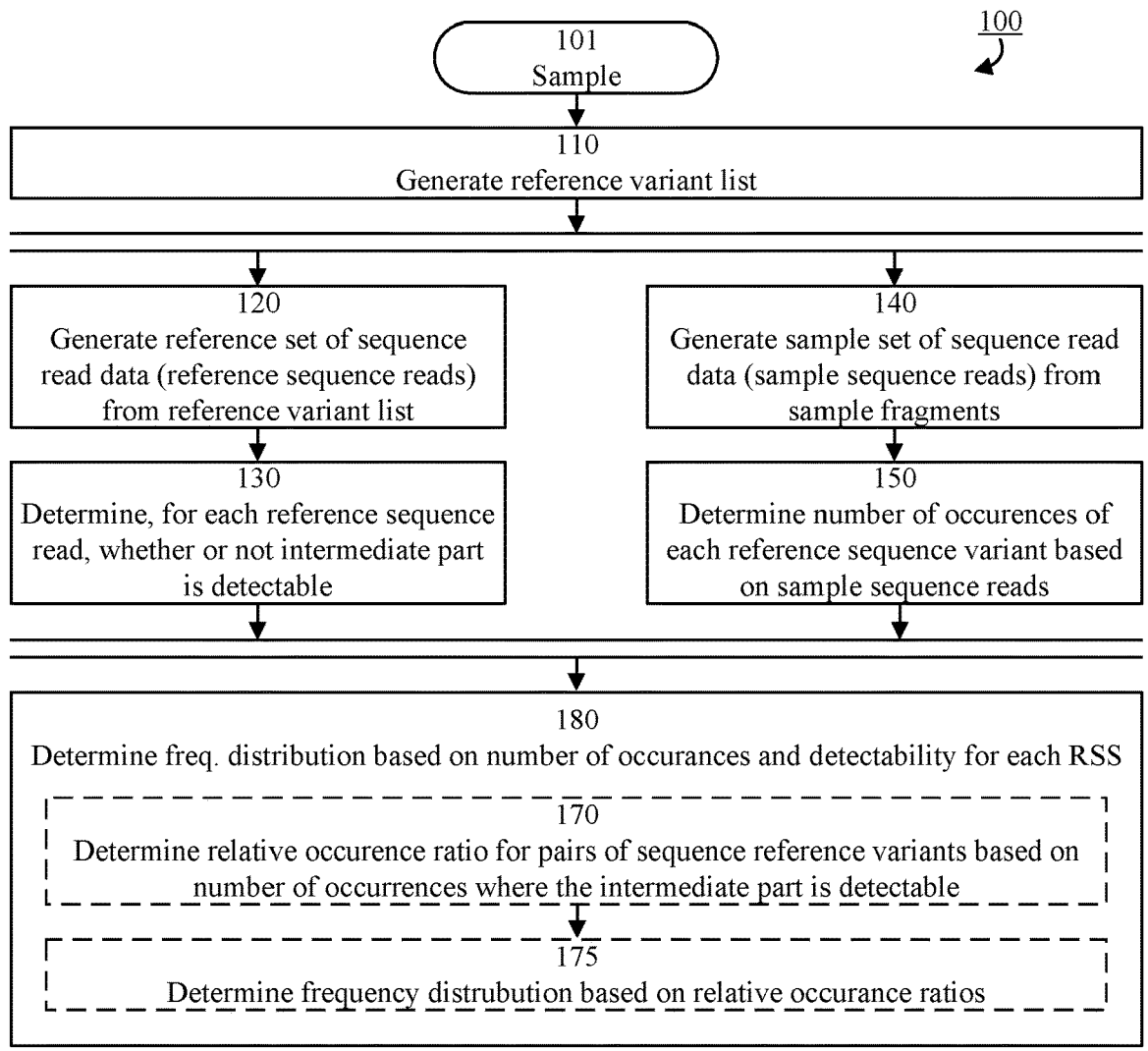
FIG. 1 is a flowchart illustrating example method steps according to some embodiments.

FIG. 1 illustrates an example method 100 according to some embodiments for determining a frequency distribution of a plurality of nucleotide sequence variants of a nucleotide sequence sample 101. In some embodiments, the method is initiated by receiving an input signal indicative of the plurality of nucleotide sequence variants and/or the nucleotide reference sequence.

A reference variant list of sequence reference variants is generated in step 110. The reference variant list comprises (e.g., consists of) unique nucleotide sequence variants of the plurality of nucleotide sequence variants. For example, the reference variant list may consist of all unique nucleotide sequence variants of the plurality of nucleotide sequence variants, or a sub-set thereof. Thus, when there are two or more identical nucleotide sequence variants in the plurality, only one of them is typically entered in the reference variant list.

The reference variant list may be generated using any suitable approach. For example, the reference variant list may be generated from the nucleotide sequence sample 101 by performing next generation sequencing (NGS) to produce NGS read data, and de-novo alignment of the NGS read data relative the nucleotide reference sequence to identify all intermediate parts, followed by a cleanup process to provide the reference variant list.

In step 120, a reference set of sequence read data is generated by performing a plurality of reference sequence reads for each sequence reference variant of the reference variant list. Each reference sequence read has a read start site (RSS) indicating where in the sequence reference variant the read starts. The read start site may, for example, be defined in relation to the location of the intermediate part of the sequence reference variant. Alternatively, the read start site may be defined in relation to another location (e.g., the start or the end) of the sequence reference variant.

In typical embodiments, each reference sequence read also has a length and/or a direction. The length may, for example, define the number of nucleotide sequence units (e.g., base pairs) to be processed in a read, or the number of nucleotide sequence units (e.g., base pairs) matching the nucleotide reference sequence in a read. The length may, typically but not necessarily, be equal for all reference sequence reads. The direction may be one of a forward direction and a reverse direction.

In a typical example, step 120 comprises performing, for each sequence reference variant of the reference variant list, one forward reference sequence read for each possible RSS of the sequence reference variant and one reverse sequence read for each possible RSS of the sequence reference variant.

In step 130, it is determined (for each RSS and for the intermediate part of each sequence reference variant) whether or not the intermediate part is detectable by a corresponding reference sequence read (i.e., a reference sequence read of the sequence reference variant starting at the RSS).

Typically, only some (or none) of the reference sequence reads extend over the entire intermediate part, However, the intermediate part may be detectable for reference sequence reads that extend over the start or the end of the intermediate part (a bridge point between the coinciding part of the variant and the intermediate part of the variant) such that the intermediate part can be uniquely recognized.

The determination is based on alignment of the corresponding reference sequence read to the reference variant list. Alignment may be achieved using any suitable alignment tool. The alignment may, typically, provide a detection metric (e.g., a detection correlation or a detection quality score) value for each reference sequence read, wherein the detection metric value is indicative of how well the reference sequence read matches a particular part (variant and RSS) of the reference variant list.

Furthermore, there may be defined a detection threshold value, which may be static or may be dynamically variable. Typically, a high detection metric value indicates a good match. Step 130 may then comprise determining an intermediate part to be detectable at an RSS by the corresponding reference sequence read when the detection metric value is above the detection threshold value, and determining the intermediate part to be non-detectable at the RSS by the corresponding reference sequence read otherwise.

In other embodiments, a low detection metric value indicates a good match and step 130 may then comprise determining an intermediate part to be detectable at an RSS by the corresponding reference sequence read when the detection metric value is below the detection threshold value, and determining the intermediate part to be non-detectable at the RSS by the corresponding reference sequence read otherwise.

Determining detectability based on the alignment may be termed mapping.

In step 140, a sample set of sequence read data is generated by performing one or more sample sequence reads for each of a plurality of nucleotide sequence variant fragments of the nucleotide sequence sample.

The plurality of nucleotide sequence variant fragments of the nucleotide sequence sample may be produced in any suitable way. For example, the nucleotide sequence sample may be subjected to amplification in a sample preparation process, followed by a NGS library fragmentation and labeling.

Each sample sequence read corresponds to a reference sequence read and has a corresponding RSS indicating where in the fragment the read starts. Similarly as mentioned above, each sample sequence read may also have a length and/or a direction.

The one or more sample sequence reads for each nucleotide sequence variant fragment may typically comprise a forward read from the start of the fragment and/or a reverse read from the end of the fragment.

In step 150, a total number of occurrences in the sample set is determined for each RSS and for the intermediate part of each sequence reference variant, i.e., how many times each sequence reference variant appears in the sample set for each RSS.

The determination is based on alignment of the corresponding sample sequence read to the reference variant list. Alignment may be achieved using any suitable alignment tool. The alignment may, typically, provide a sample metric (e.g., a sample correlation or a sample quality score) value for each sample sequence read, wherein the sample metric value is indicative of how well the sample sequence read matches a particular part (variant and RSS) of the reference variant list.

Furthermore, there may be defined an occurrence threshold value, which may be static or may be dynamically variable.

Typically, a high sample metric value indicates a good match. Step 150 may then comprise counting an occurrence when the sample metric value is above an occurrence threshold value, and refraining from counting an occurrence otherwise.

In other embodiments, a low sample metric value indicates a good match and step 150 may then comprise counting an occurrence when the sample metric value is below an occurrence threshold value, and refraining from counting an occurrence otherwise.

Determining the total number of occurrences based on the alignment may also be termed mapping.

As illustrated in FIG. 1, steps 120 and 130 may be performed in parallel with steps 140 and 150. However, this not intended as limiting and, in other embodiments, one or more of the steps 140 and 150 may be performed in sequence with one or more of the steps 120 and 130. For example, all of the steps 120, 130, 140 and 150 may be performed in sequence according to some embodiments.

In step 180, the frequency distribution is determined of the plurality of nucleotide sequence variants based on the total number of occurrences and the determination of whether or not the intermediate part is detectable for each RSS. This determination may, for example, be performed via optional steps 170 and 175 as exemplified below.

In step 170 a relative occurrence ratio is determined for each pair of sequence reference variants which does not comprise the nucleotide reference sequence. The ratio is determined based on the number of occurrences of each of the sequence reference variants of the pair determined for an RSS where the intermediate part is detectable for each of the sequence reference variants of the pair.

For example, for a pair consisting of a first sequence reference variant and a second sequence reference variant, the following process may be performed in step 170:

Check for each RSS if the intermediate parts of the first and second sequence reference variants are detectable at the RSS.

If one or both are un-detectable at the RSS, an intermediate relative occurrence ratio is undefined at the RSS.

If both are detectable, calculate an intermediate relative occurrence ratio for the RSS as a ratio between the total number of occurrences for the first sequence reference variant and the total number of occurrences for the second sequence reference variant.

Let the relative occurrence ratio for the pair be defined as a (possibly weighted) average, over the RSS where both are detectable, of the intermediate relative occurrence ratios.

In step 175 the frequency distribution of the plurality of nucleotide sequence variants is determined based on the relative occurrence ratios.

In some embodiments, the method may also comprise transferring a reporting signal indicative of the frequency distribution to a user interface.

Figures 2, 3:
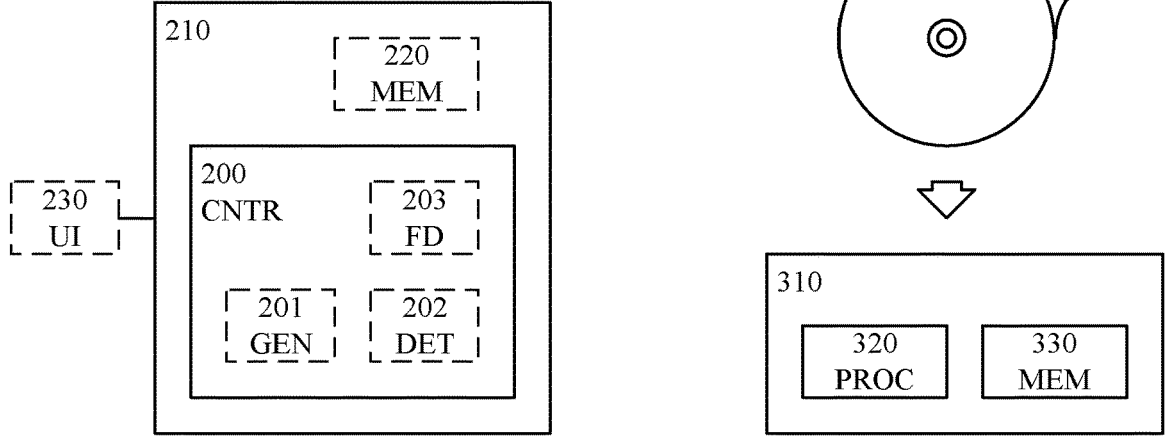
FIG. 2 is a schematic block diagram illustrating an example apparatus according to some embodiments.
FIG. 3 is a schematic drawing illustrating an example computer readable medium according to some embodiments.

FIG. 2 schematically illustrates an example apparatus 210 according to some embodiments. The apparatus 210 may, for example be included in a server node. Furthermore, the apparatus 210 may be adapted to cause execution of one or more method steps as described in connection with FIG. 1. For example, the apparatus 210 may be adapted to execute one or more method steps as described in connection with FIG. 1.

The apparatus is for determining a frequency distribution of a plurality of nucleotide sequence variants of a nucleotide sequence sample, wherein the plurality of nucleotide sequence variants comprises a nucleotide reference sequence, and wherein each nucleotide sequence variant (which is not identical to the nucleotide reference sequence) differs from the nucleotide reference sequence by at least one intermediate part and coincides with the nucleotide reference sequence by at least two parts of the nucleotide reference sequence.

The apparatus 210 comprises controlling circuitry (CNTR; e.g., one or more processors) 200. The apparatus 210 may also comprise memory circuitry (MEM) 220 which may be connected to, or otherwise associated with, the controlling circuitry 200. Furthermore, the apparatus 210 may comprise, or be associated with (e.g., connected to), user interface circuitry and/or a user interface apparatus (UI) 230.

The controlling circuitry 200 is configured to cause generation of a reference variant list of sequence reference variants comprising unique nucleotide sequence variants of the plurality of nucleotide sequence variants (compare with step 110 of FIG. 1), and generation of a reference set of sequence read data by performing a plurality of reference sequence reads for each sequence reference variant of the reference variant list, wherein each reference sequence read has a read start site (compare with step 120 of FIG. 1). The controlling circuitry 200 is also configured to cause generation of a sample set of sequence read data by performing one or more sample sequence reads for each of a plurality of nucleotide sequence variant fragments of the nucleotide sequence sample, wherein each sample sequence read corresponds to a reference sequence read and has a corresponding read start site (compare with step 140 of FIG. 1).

To this end the controlling circuitry 200 may comprise, or be otherwise associated with, generating circuitry (GEN; e.g. a generator) 201 configured to generate one or more of: the reference variant list, the reference set, and the sample set.

The controlling circuitry 200 is further configured to cause (for each RSS and for the intermediate part of each sequence reference variant) determination of whether or not the intermediate part is detectable by corresponding reference sequence read based on alignment of the corresponding reference sequence read to the reference variant list (compare with step 130 of FIG. 1), and determination of a total number of occurrences in the sample set of sequence read data based on alignment of corresponding sample sequence read to the reference variant list (compare with step 150 of FIG. 1).

To this end the controlling circuitry 200 may comprise, or be otherwise associated with, determination circuitry (DET; e.g. a determiner) 202 configured to determine one or more of: detectability and total number of occurrences of the intermediate parts.

The controlling circuitry 200 is also configured to cause determination of the frequency distribution of the plurality of nucleotide sequence variants based on the total number of occurrences and the determination of whether or not the intermediate part is detectable for each RSS (compare with step 180 of FIG. 1).

To this end the controlling circuitry 200 may comprise, or be otherwise associated with, frequency determination circuitry (FD; e.g. a determiner) 203 configured to determine one or more of: relative occurrence ratios and the frequency distribution.

The memory circuitry 220 may be configured to store one or more of: the plurality of nucleotide sequence variants, the nucleotide reference sequence, the frequency distribution, and any intermediate information or result as described herein.

The user interface circuitry/apparatus 230 may be configured to obtain, from a user, information including the plurality of nucleotide sequence variants and/or the nucleotide reference sequence, and transfer the received information to the apparatus 210 via an input signal indicative of the information.

In various embodiments, the user interface circuitry/apparatus 230 may also be configured to obtain, from the user, the target position (target site, site of interest) relative to which the analysis is carried out.

In some embodiments, the user interface circuitry/apparatus 230 may also be configured to obtain, from the user, various other analysis preference parameters. Examples of such parameters include:
one or more threshold values (e.g., a value of a threshold for alignment quality),
a length of safety boundaries ranging from the edges of detectability regions,
a normalization type and a number of normalization steps, and
other robustness parameters.

Alternatively or additionally, the user interface circuitry/apparatus 230 may be configured to receive a reporting signal indicative of the frequency distribution from the apparatus 210, and process the reporting signal for providing a representation of the frequency distribution for access by the user.

Generally, the user interface circuitry/apparatus 230 may be replaced by, complemented by, or generalized to other suitable interface circuitry/apparatus. For example, the frequency distribution may not be directly provided to a user via user interface circuitry 230, but may instead be provided to other circuitry for use of the frequency distribution. Alternatively or additionally, the frequency distribution may be directly provided to a user via user interface circuitry 230 and may be provided to the other circuitry via the user.

In some typical examples, the other circuitry may be one or more of calculation/processing circuitry using the frequency distribution as a parameter, selection circuitry configured to make a selection based on the frequency distribution, and adaptation circuitry configured to adapt a process based on the frequency distribution.

Generally, the frequency distribution may be used for processing/selection/adaptation relating to various biological applications. A few illustrative examples of such application will be given in the following.

In a first example, it is a goal to stratify sequence variation implications for a given sample within gene editing research as an area of application. In this example, an input may be the total variant distribution of a sample and the procedure may comprise determining frequencies of non-original reference sequence variants compared to the original (first) reference sequence frequency with the following indications:

1. The degree of total sequence variation at the position of interest (if percent modification is above threshold 10%, at low, medium and high intervals of 20%, or other user defined parameters).
2. The degree of sequence essentiality at the position (if percent Open Reading Frame (ORF) break is above 70% essentiality is negative or if % ORF break is below 70% essentiality is positive, at low, medium and high degrees of 10%, or other user defined parameters).
3. The degree reference sequence variant diversity (if number of variants is low, medium, or large at intervals of [below 5, between 5-15, above 15, respectively], or other user defined parameters).
4. Whether there exist preferred reference sequence variants (if relative reference variant frequency is above 10% of total reference variant frequency, or another user defined parameter).
5. If there exists a preferred reference sequence variant, a) print for the user the intermediate altered sequence to the user, b) together with print of the full variant reference sequence, and if user provided the protein coding sequence correlation with the original reference sequence—c) provide a print of the new altered protein coding sequence due to the intermediate variant coding sequence.

In a second example, it is a goal to stratify preferred reference sequence variants for a given sample within gene editing research as an area of application. For example:

1. Identification of a critical protein coding region along the analyzed reference sequence responding to the experimental design.
2. Identification of a critical regulatory region along the analyzed reference sequence responding to the experimental design.

In this example, an input may be the total variant distributions of a sample or a set of samples and the procedure may comprise determining frequencies of non-original reference sequence variants compared to the original (first) reference sequence frequency with the following indications:

1. If there exist one or more preferred reference sequence variants (for which the relative reference variant frequency is above 10% of total reference variant frequency, or another user defined parameter), then the preferred reference sequence variants must be separated and printed to the user, indicating for each preferred reference sequence variant:
   a. The preferred reference sequence variant intermediate sequence, and the full-length reference sequence variant.
   b. Current relative and absolute reference sequence variant frequency.
   c. If the user provided reference sequence protein coding sequence, then a printout of the predicted reference sequence variant encoded protein coding sequence.
   d. If the user provided original reference sequence annotated with regulatory recognition sites, then a printout of the predicted affected regulatory sites that are unique to the intermediate sequence of the preferred reference sequence variant that do not appear in the list of non-preferred reference sequence variant intermediate sequences.
2. If there exist a set of more than one samples for which one of more samples contains preferred reference sequence variants (for which the relative reference variant frequency is above 10% of total reference variant frequency, or another user defined parameter), where one or more of the samples are subjected to different experimental designs then for each sample, the preferred reference sequence variants must be separated and printed to the user, indicating for each preferred reference sequence variant:
   a. The preferred reference sequence variant intermediate sequence, and the full-length reference sequence variant.
   b. Current relative and absolute reference sequence variant frequency.
   c. If the user provided reference sequence protein coding sequence, then a printout of the predicted reference sequence variant encoded protein coding sequence.
   d. If the user provided original reference sequence annotated with regulatory recognition sites, then a printout of the predicted affected regulatory sites that are unique to the intermediate sequence of the preferred reference sequence variant that do not appear in the list of non-preferred reference sequence variant intermediate sequences.
   e. If the user provided comparison groups for samples such that several samples comprise two or more groups, the user can receive a printout of preferred reference sequence variant types present in the different groups, with possible subdivisions:
      i. Unique reference sequence variants for each group with their relative and absolute frequency.
      ii. Common reference sequence variants for all groups with their relative and absolute frequency per group.
      iii. Shared reference sequence variants for specific pairwise combinations of groups with their relative and absolute frequency per group.

In a third example, it is a goal to stratify experimental design for a set of samples within gene editing research as an area of application. For example:
1. Selection of the most appropriate sgRNA for a CRISPR editing experiment (e.g. sgRNA1, sgRNA2, or sgRNA3).
2. Selection of the best editing time in a gene editing experiment (e.g. immediately post cell thawing, 24 hours after cell thawing, or 48 hours after cell thawing).
3. Selection of the best editing modality (e.g. use of Cas9 protein with sgRNA, or Cas9 mRNA with sgRNA).

In this example, an input may be the total variant distributions of several user submitted samples that can be analyzed serially (or in parallel on multiple computing nodes/machines), and the procedure may comprise comparison of the total reference sequence variant distribution frequencies between samples with the following indications:
1. If the samples compare different experimental conditions, indicate to user if the samples underwent successful modification (if percent modification is above threshold 10%, or another user defined parameter).
2. The ranking of experiment designs (e.g. if one or more of the samples underwent successful modification, stratify the successful samples from the unsuccessful ones and rank and print the successful ones by percentage of total modification, then indicate to the user the best experimental design). The ranking of successful experimental designs can be carried our based-on user defined parameter such as: total sequence variation, degree of sequence essentiality, degree of variant diversity, number of preferred variants, or uniqueness of preferred variants.

In a fourth example, it is a goal to stratify degree of variation in a sample within clinical analysis of a genetic sample as an area of application. For example:
1. Evaluation of reduction in a particular reference variant frequency for treatment result testing or validation.
2. Follow up to treatment for monitoring against expansion of any reference sequence variant frequency.

In this example, an input may be the total variant distribution of a sample and the procedure may comprise evaluation of the non-original reference sequence variant frequencies compared to original (first) reference sequence frequency with the following indications:
1. If user did not input a previous of predicted set of sample variants, and if the degree of total sample sequence variation is above user defined threshold (e.g. 0.1%, or another user defined parameter), user will be notified the degree to which any discovered variant is present in the sample (e.g. low if under 1%, medium 1%-5%, and high >5%, or other user defined parameters).
2. If a user inputs a previous or predicted set of sample variants, and in comparison, to this input set, at the end of the analysis the relative variant frequency of any previously identified variant has changed (above or below a user defined threshold level, e.g. 2%), the altered reference sequence variants must be separately printed to the user, indicating for each altered reference sequence variant:

a. The reference sequence variant intermediate sequence, and if user provided reference protein coding sequence, then the variant encoded predicted protein coding sequence.
b. Previous relative and absolute reference sequence variant frequency.
c. Current relative and absolute reference sequence variant frequency.

3. If a user inputs a previous or predicted set of sample variants, and in comparison, to this input set, at the end of the analysis there are additional or fewer sequence variants (above a user defined threshold level, e.g. 0.1%), the missing reference sequence variants and the newly discovered reference sequence variants must be separately printed to the user, indicating for each reference sequence variant:
   a. The reference sequence variant intermediate sequence, and if user provided reference protein coding sequence, then the variant encoded predicted protein coding sequence.
   b. Previous relative and absolute reference sequence variant frequency.
   c. Current relative and absolute reference sequence variant frequency.

Additional data stratification points that may be executed during the analysis:
1. After the alignment and as a condition for the mapping the reads are tested individually for:
   a. Read length above user specified length (e.g. 151 bases). Only reads with identical length are further processed.
   b. Read alignment quality above a user specified score (e.g. 10, or another user defined parameter). Only reads with an appropriate quality score are further processed.
   c. Read alignment matching is user specified (e.g. "151M", or another user defined parameter). Only reads with an appropriate alignment are further processed.
2. After analysis reference sequence variants are evaluated for their absolute frequency in the sample, against a user defined threshold parameter, below which the reference sequence variant is deemed a contaminant, does not pass final quality analysis, and is removed from the final set of user-reported variants.

According to some embodiments, a computer program product comprises a computer readable medium such as, for example a universal serial bus (USB) memory, a plug-in card, an embedded drive or a read only memory (ROM). FIG. 3 illustrates an example computer readable medium in the form of a compact disc (CD) ROM 300. The computer readable medium has stored thereon a computer program comprising program instructions. The computer program is loadable into a data processor (PROC) 320, which may, for example, be comprised in a server node 310 or may be distributed throughout several server nodes in a cloud based implementation. When loaded into the data processing unit, the computer program may be stored in a memory (MEM) 330 associated with or comprised in the data-processing unit. According to some embodiments, the computer program may, when loaded into and run by the data processing unit, cause execution of method steps according to, for example, one or more of the method steps illustrated in FIG. 1 or otherwise described herein.

Figure 4:
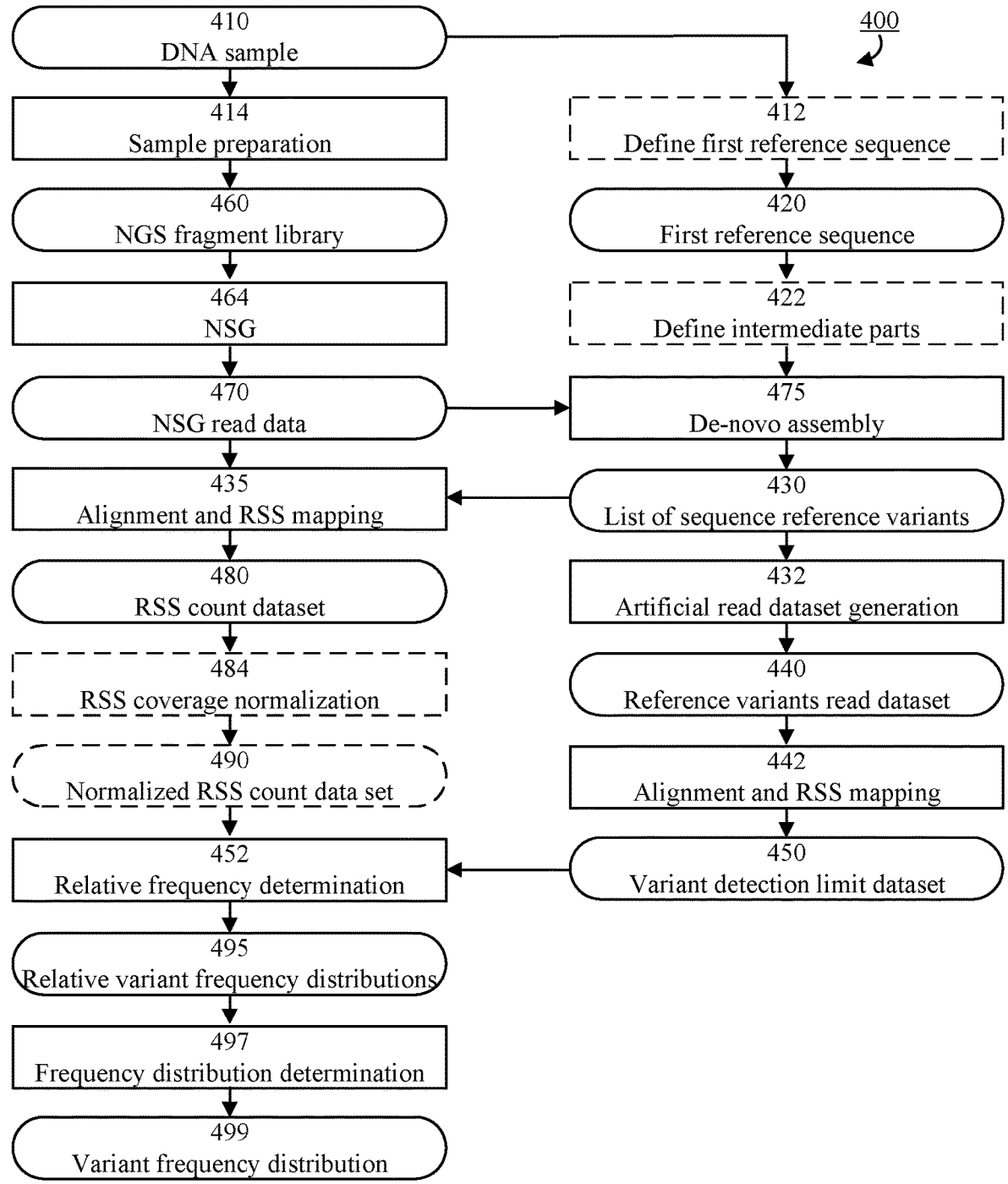
FIG. 4 is a flowchart illustrating example method steps according to some embodiments.
Figure 5:
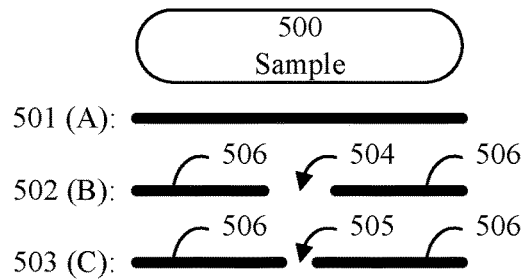
FIGS. 5 and 6 are schematic drawing illustrating example parts of a process according to some embodiments.
Figure 5:
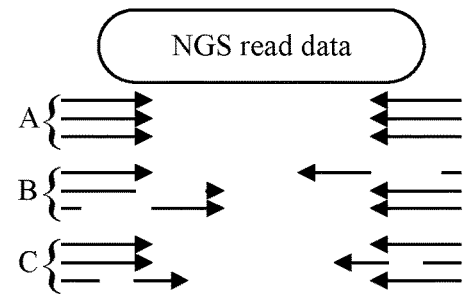
Figure 5:
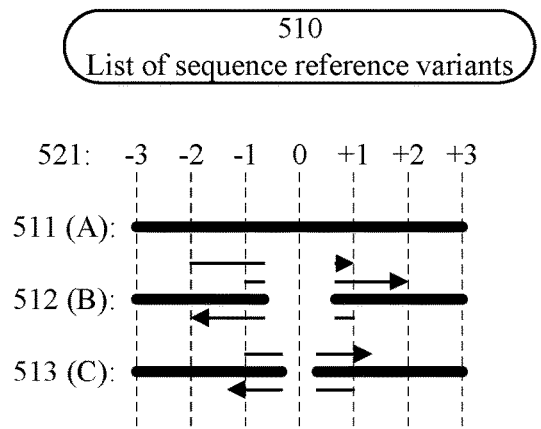
Figure 5:
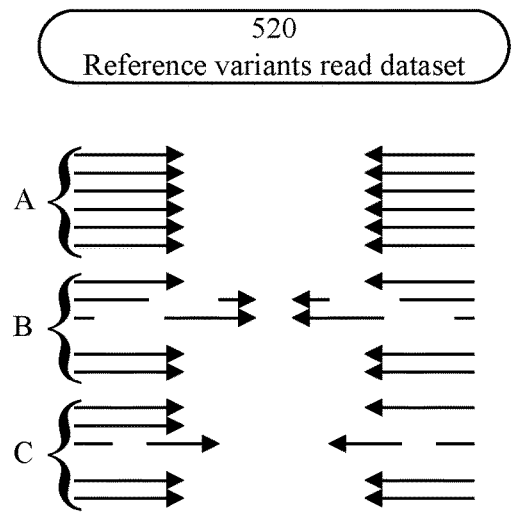
Figure 5:
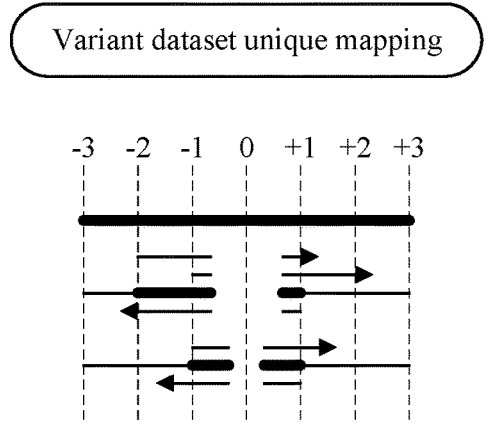
Figure 5:
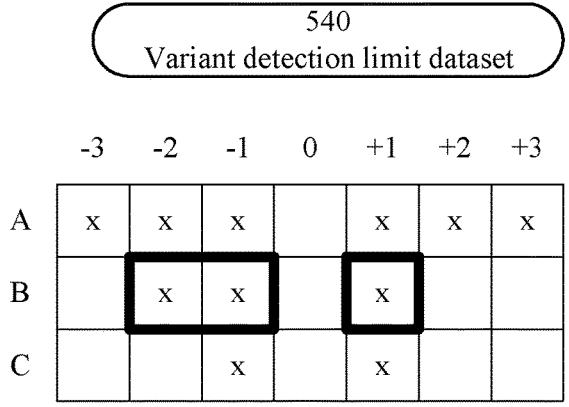
Figure 6:
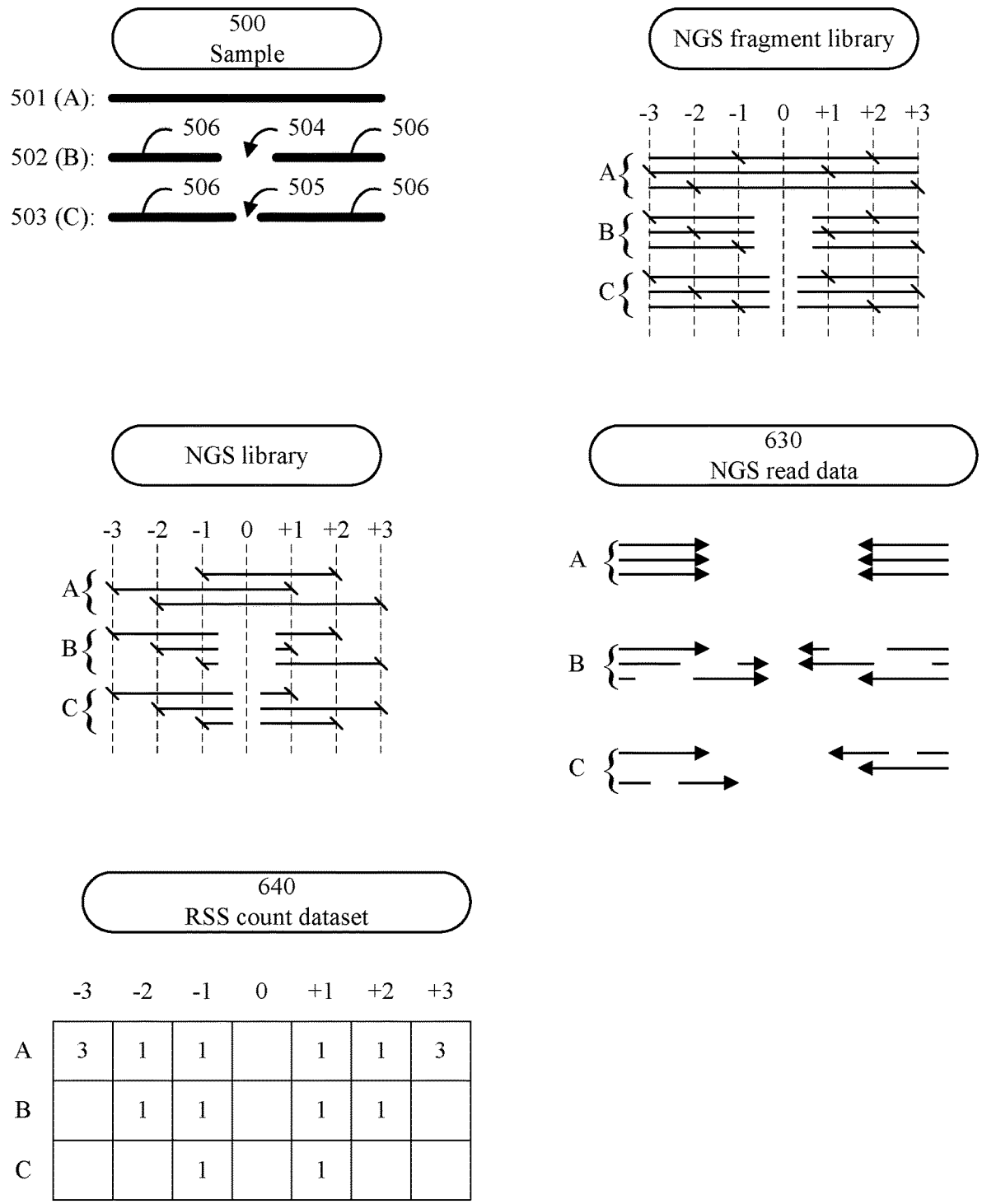

FIG. 4 illustrates an example method 400 according to some embodiments, and will be explained in association with the schematic illustrations of FIGS. 5 and 6. FIGS. 4-6 may be seen as an example way to implement the method of FIG. 1. DNA is used as an example of nucleotide sequence in the following.

The method 400 is executed in relation to a DNA sample 410, 500 for determining a frequency distribution of a plurality of DNA variants of the DNA sample. For simplicity, only three DNA variants (A, B, C) 501, 502, 503, respectively, are illustrated. In the DNA sample there may be one or more instances of each of the DNA variants.

The DNA variants (A, B, C) 501, 502, 503 are relative to a target position "0" of the reference sequence. The target position is the position around which the analysis is carried out and it is part of the definition of the reference sequence. A sample set of sequence read data is generated according to any suitable process (compare with step 140 of FIG. 1). For example, sample preparation 414 (possibly including polymerase chain reaction, PCR) may provide an amplified target region, and NGS library fragmentation may provide an NGS fragment library 460 which after library labeling is termed an NGS library (plurality of nucleotide sequence variant fragments). Next generation sequencing (NGS) 464, which includes forward and reverse reads (sample sequence reads) of the NGS library, may provide NGS read data 470, 630 as an example of the sample set.

The plurality of DNA variants comprises a DNA variant (A) 420, 501 used as reference DNA (i.e., a nucleotide reference sequence). The nucleotide reference sequence may also be termed the first reference nucleotide sequence or the first reference sequence. As mentioned above, the first reference nucleotide sequence may be pre-defined (e.g., by a user) or may be defined as part of the method 400 as illustrated by optional step 412.

Each DNA variant which is not identical to the reference DNA (i.e., B, 502, and C, 503) differs from the reference DNA by at least one intermediate part, 504, 505, and coincides with the reference DNA by at least two parts 506 of the reference DNA. As mentioned above, the intermediate part may be an indel, an insertion, a deletion, an alteration or a translocation, for example. For simplicity the intermediate parts are illustrated as deletions in this example. The method may comprise studying all intermediate parts of the sample, or only some defined intermediate parts. Which intermediate parts to include may be pre-defined (e.g., by a user) or may be defined as part of the method 400 as illustrated by optional step 422.

When it is determined which intermediate parts to include, a reference variant list, 430, 510, of sequence reference variants is generated (compare with step 110 of FIG. 1). The reference variant list typically comprises (one, and only one, instance of) unique DNA variants, 511, 512, 513, of the plurality of DNA variants 501, 502, 503; e.g., all unique DNA variants, or unique DNA variants corresponding to the defined (e.g., in step 422) intermediate parts. The reference variant list 430 may be generated, for example, via de-novo assembly/alignment (including cleanup) based on the NGS read data as illustrated by step 475.

A reference set (reference variants read dataset), 440, 520, of sequence read data is generated (compare with step 120 of FIG. 1) by performing a plurality of reference sequence reads (artificial read dataset generation) for each sequence reference variant of the reference variant list as illustrated in step 432. Each reference sequence read has a read start site RSS) 521 as elaborated on earlier.

Via alignment and mapping of reference sequence reads to the reference variant list as illustrated by step 442, it is determined, for each RSS and for the intermediate part of each sequence reference variant, whether or not the intermediate part is detectable by corresponding reference sequence read based on alignment (compare with step 130 of FIG. 1). This process results in a variant detection limit dataset 450, 540, which indicates for each RSS and intermediate part if the intermediate part is detectable at the RSS (illustrated as marked by "x" in FIG. 5, 540) or not (illustrated as empty in FIG. 5, 540). The bold boxes in FIG. 5, 540 may be termed the detection limit for DNA variant B.

Via alignment and mapping of sample sequence reads (NGS read data) 470 to the reference variant list 430 as illustrated by step 435, a total number of occurrences (an RSS count dataset), 480, 640, is determined for each RSS and for the intermediate part of each sequence reference variant (compare with step 150 of FIG. 1). In FIG. 6, 640, "1" could, of course be replaced with any positive integer in accordance with the number of occurrences registered. Optionally, the RSS count dataset may be normalized as illustrated by step 484, resulting in a normalized RSS count data set 490. Normalization may, for example, be over each RSS or over each sequence reference variant.

Relative variant frequency distributions (relative occurrence ratios) 495 are determined in step 452 (compare with step 170 of FIG. 1) for each pair of DNA variants which does not comprise the reference DNA. For the example in FIGS. 5 and 6, the relative occurrence ratios between B and C may be determined as follows:

RSS (−3, +2, +3): Intermediate relative occurrence ratio undefined since none of B and C are detectable (see 540).

RSS (−2): Intermediate relative occurrence ratio undefined since C is not detectable (see 540).

RSS (−1, +1): Both B and C detectable. Intermediate relative occurrence ratios defined as 1/(1+1)=50%.

The defined intermediate relative occurrence ratios may, of course, differ in a general scenario. If so, the relative occurrence ratio for a pair of DNA variants may be determined as an average over RSS of the defined intermediate relative occurrence ratios (possibly weighted in relation to the number of occurrences for each RSS).

The frequency distribution 499 is then determined as illustrated in step 497 (compare with step 180 of FIG. 1). First, an intermediate relative frequency of the reference DNA may be determined for each RSS where any non-reference sequence variant is detectable as elaborated on above. Then, a relative frequency of the reference DNA may be defined as an average over the RSS (possibly weighted in relation to the number of occurrences for each RSS). The frequency distribution may be determined based on the relative occurrence ratios for each pair and the relative frequency of the reference DNA.

An alternative description of an approach to determining the frequency distribution may be described as follows:

For each RSS where both B and C are detectable, calculate $X_B/X_C$, where $X_B$ denotes the total number of occurrences for the variant sequence B and $X_C$ denotes the total number of occurrences for the variant sequence C, and repeat for all pairs of variants that are not the reference variant sequence A.

Normalize the set $(X_i/X_B, X_i/X_C, \ldots)$ for each particular variant sequence i (e.g., B, C, etc.).

Average over all normalized sets to give a relative frequency estimate for each variant.

Yet an alternative description of an approach to determining the frequency distribution may be described as follows:

1. Given RSS count dataset.
2. For each variant (e.g. variant A) in the list of reference sequence variants, divide the RSS vector of variant A by the RSS vector of another variant (e.g., variant B) in the list of reference sequence variants (e.g., A-Z), such that the division results are recorded only within when both variants (e.g., A and B) are detectable. From this output vector, remove all trivial or non-defined results (typically: nan, 0, 1, −inf, +inf) to get a set of estimator points for the comparison of A to B, and record the average of the set. Proceed with all other variants (e.g., variants C-Z) in the list of reference sequence variants until a column set (all/A) is complete. Then repeat the entire process under item 2 for all variants (e.g, B-Z).
3. For each of the column sets (e.g. all/A, all/B, etc.) divide the respective column set by the first column set (all/A) to get a relative set scaling factor. Divide the column set by the scaling factor to get a scaled column set.
4. When all column sets are scaled to first column set (all/A), proceed to average every row of the scaled dataset such that each row average is the relative average of the respective variant (row 1 is the average frequency of variant A, row 2 is the average frequency of variant B, etc.). Note that the average for each row is the relative average of only the observed non-zero data points per that row.
5. Normalize the final observed variant frequency column to 100% such that each variant is given its relative frequency out of the total observed variant count of the column.
6. During the normalization, record the number of averaging points per variant such that
    if a variant does not have any other vector division partners in its detectable range or has very few (e.g., <5) estimator points per vector division with other division partners
    it is termed an isolated variant. Next carry out the isolated variant vector division, after the above general non-isolated variant frequency normalization, with the original (first) reference sequence variant vector partner only, such that the division is only in the range where no other variants are detectable.
7. Then carry out the isolated variant division product as before (see item 2) and add it to the previous distribution of variants, in supplement to the previously calculated 100% general non-isolated variant frequency (e.g. non-isolated 100%+new isolated 10%=110%), followed by renormalization to a new 100% relative reference sequence variant frequency distribution.
8. With the relative frequency distribution determined, calculate the first original reference sequence vector such that, for each RSS, the first reference sequence count is transformed into the first reference sequence frequency as follows:

$$\%FirstRef(RSS) = \frac{FirstRefcount(RSS)}{1 + VariantTotcount(RSS) * \left( \frac{\%VarUndetectable(RSS)}{\%VarDetectable(RSS)} \right)}$$

9. The first reference sequence vector is then averaged to give the final absolute first reference sequence frequency, which together with the remaining, adjusted, variant frequency distribution calculated before (see item 7) completes the absolute variant frequency distribution.

As mentioned above, existing approaches for estimation of sequence variant frequency distribution may be proved to be inaccurate; at least to some extent. For example, many existing approaches make one or more of the following assumptions (which may not always hold true):

PCR amplification from genomic DNA is unbiased.

Library fragmentation (e.g., tagmentation) of amplified DNA is uniform.

All variant types are detected by all reads.

Variant alignment (quality score) of all variant types is uniform.

Under the above assumptions, a hypothesis may be that all events (detection of an indel) have the same likelihood and, therefore, that summing all detected insertions and deletions (indels) and all wild type (WT) reads provides an average of the local indel distribution at the locus.

Embodiments presented herein are adjusted to situations where one or more of the above assumptions are faulty. For example, the library fragmentation is typically not uniform, but is often subject to a bias.

The described embodiments and their equivalents may be realized in software or hardware or a combination thereof. The embodiments may be performed by general purpose circuitry. Examples of general purpose circuitry include digital signal processors (DSP), central processing units (CPU), co-processor units, field programmable gate arrays (FPGA) and other programmable hardware. Alternatively or additionally, the embodiments may be performed by specialized circuitry, such as application specific integrated circuits (ASIC). The general purpose circuitry and/or the specialized circuitry may, for example, be associated with or comprised in an apparatus such as a server node (e.g., distributed to several server nodes in a cloud-based implementation).

Embodiments may appear within an electronic apparatus (such as a server node) comprising apparatuses, arrangements, circuitry, and/or logic according to any of the embodiments described herein. Alternatively or additionally, an electronic apparatus may be configured to perform methods according to any of the embodiments described herein.

Generally, all terms used herein are to be interpreted according to their ordinary meaning in the relevant technical field, unless a different meaning is clearly given and/or is implied from the context in which it is used.

Reference has been made herein to various embodiments. However, a person skilled in the art would recognize numerous variations to the described embodiments that would still fall within the scope of the claims.

For example, the method embodiments described herein discloses example methods through steps being performed in a certain order. However, it is recognized that these sequences of events may take place in another order without departing from the scope of the claims. Furthermore, some method steps may be performed in parallel even though they have been described as being performed in sequence. Thus, the steps of any methods disclosed herein do not have to be performed in the exact order disclosed, unless a step is explicitly described as following or preceding another step and/or where it is implicit that a step must follow or precede another step.

In the same manner, it should be noted that in the description of embodiments, the partition of functional blocks into particular units is by no means intended as limiting. Contrarily, these partitions are merely examples. Functional blocks described herein as one unit may be split into two or more units. Furthermore, functional blocks described herein as being implemented as two or more units may be merged into fewer (e.g. a single) unit.

Any feature of any of the embodiments disclosed herein may be applied to any other embodiment, wherever suitable. Likewise, any advantage of any of the embodiments may apply to any other embodiments, and vice versa.

Hence, it should be understood that the details of the described embodiments are merely examples brought forward for illustrative purposes, and that all variations that fall within the scope of the claims are intended to be embraced therein.

The invention claimed is:

1. A method for determining a frequency distribution of a plurality of nucleotide sequence variants of a nucleotide sequence sample, wherein the plurality of nucleotide sequence variants comprises a nucleotide reference sequence, and wherein each nucleotide sequence variant is not identical to the nucleotide reference sequence, and differs from the nucleotide reference sequence by at least one insertion, deletion, or translocation, the method comprising:

performing sequencing to generate a library of sequence reference variants comprising a plurality of unique nucleotide sequence variants;

generating an artificial reference set of sequence read data by performing a plurality of artificial reference sequence reads using sequencing for each sequence reference variant of the library, wherein each artificial reference sequence read has a defined read start site, RSS;

for each sequence reference variant, determining whether or not the at least one insertion, deletion, or translocation is detectable by a corresponding artificial reference sequence read by performing an alignment of the corresponding artificial reference sequence read to the library of sequence reference variants;

performing sequencing to generate a sample set of sequence read data by performing one or more sample sequence reads for each of a plurality of nucleotide sequence variant fragments of the nucleotide sequence sample, wherein each sample sequence read corresponds to an artificial reference sequence read and has a corresponding defined RSS;

for each sequence reference variant, determining a total number of occurrences of the variant in the sample set of sequence read data by performing an alignment of the corresponding sample sequence read to the sequence reference variants of the library; and determining the frequency distribution of the plurality of nucleotide sequence variants based on the total number of occurrences and the determination of whether or not the insertion, deletion, or translocation is detectable for each defined RSS.

2. The method of claim 1, further comprising defining the nucleotide reference sequence.

3. The method of claim 1, wherein determining the frequency distribution of the plurality of nucleotide sequence variants comprises:

determining, via alignment, a detection correlation value for the RSS between the corresponding artificial reference sequence read and the sequence reference variant;

determining the at least one insertion, deletion, or translocation to be detectable at the defined RSS by the corresponding artificial reference sequence read when the detection correlation value is above a detection threshold value; and determining the at least one insertion, deletion, or translocation to be non-detectable at the defined RSS by the corresponding artificial reference sequence read when the detection correlation value is not above the detection threshold value.

4. The method of claim 1, wherein determining the frequency distribution of the plurality of nucleotide sequence variants comprises:

determining, via alignment, a sample correlation value for the defined RSS between the corresponding sample sequence read and the sequence reference variant;

counting an occurrence when the sample correlation value is above an occurrence threshold value; and refraining from counting an occurrence when the sample correlation value is not above the occurrence threshold value.

5. The method of claim 1, further comprising receiving an input signal indicative of one or more of the plurality of nucleotide sequence variants and the nucleotide reference sequence.

6. The method of claim 1, further comprising transferring a reporting signal indicative of the frequency distribution to a user interface.

7. A method for determining a frequency distribution of a plurality of nucleotide sequence variants of a nucleotide sequence sample, wherein the plurality of nucleotide sequence variants comprises a nucleotide reference sequence, and wherein each nucleotide sequence variant is not identical to the nucleotide reference sequence, and differs from the nucleotide reference sequence by at least one insertion, deletion, or translocation, the method comprising:

performing sequencing to generate a library of sequence reference variants comprising a plurality of unique nucleotide sequence variants;

generating an artificial reference set of sequence read data by performing a plurality of artificial reference sequence reads using sequencing for each sequence reference variant of the library, wherein each artificial reference sequence read has a read start site, RSS indicating where in the sequence reference variant the artificial reference sequence read starts;

for each sequence reference variant, determining whether or not the at least one insertion, deletion, or translocation is detectable by a corresponding artificial reference sequence read by performing an alignment of the corresponding artificial reference sequence read to the library of sequence reference variants;

performing sequencing to generate a sample set of sequence read data by performing one or more sample sequence reads for each of a plurality of nucleotide sequence variant fragments of the nucleotide sequence sample, wherein each sample sequence read corresponds to an artificial reference sequence read and has a corresponding RSS;

for each sequence reference variant, determining a total number of occurrences of the variant in the sample set of sequence read data by performing an alignment of the corresponding sample sequence read to the sequence reference variants of the library; and determining the frequency distribution of the plurality of nucleotide sequence variants based on the total number of occurrences and the determination of whether or not the insertion, deletion, or translocation is detectable for each RSS.

* * * * *